United States Patent [19]

Warring et al.

[11] Patent Number: 5,402,777
[45] Date of Patent: Apr. 4, 1995

[54] METHODS AND DEVICES FOR FACILITATED NON-INVASIVE OXYGEN MONITORING

[75] Inventors: Jessica A. Warring, Millbrae; David B. Swedlow, Foster City; Michael J. N. Cormier, Mountain View; Su Il Yum, Los Altos; Lina T. Taskovich, Palo Alto; Albert Ollerdessen, Danville, all of Calif.

[73] Assignee: ALZA Corporation, Palo Alto, Calif.

[21] Appl. No.: 893,480

[22] Filed: Jun. 3, 1992

Related U.S. Application Data

[63] Continuation-in-part of Ser. No. 722,645, Jun. 28, 1991, Pat. No. 5,267,563.

[51] Int. Cl.⁶ .............................................. A61L 15/00
[52] U.S. Cl. .................................. 604/307; 128/633; 128/637; 128/666; 424/449
[58] Field of Search ............................. 128/632–633, 128/664–666, 637; 604/304, 307; 424/447–449

[56] References Cited

U.S. PATENT DOCUMENTS

| | | | |
|---|---|---|---|
| Re. 31,440 | 11/1983 | Eberhard et al. | 128/635 |
| 3,598,122 | 8/1971 | Zaffaroni . | |
| 3,598,123 | 8/1971 | Zaffaroni . | |
| 3,628,525 | 12/1971 | Polanyi et al. . | |
| 3,742,951 | 11/1972 | Zaffaroni . | |
| 3,993,073 | 11/1976 | Zaffaroni . | |
| 4,031,894 | 6/1977 | Urquhart et al. . | |
| 4,060,084 | 11/1977 | Chandrasekaran et al. . | |
| 4,144,317 | 3/1979 | Higuchi et al. | 424/21 |
| 4,201,211 | 5/1980 | Chandrasekaran et al. . | |
| 4,296,752 | 10/1981 | Welsh et al. | 128/635 |
| 4,324,256 | 4/1982 | Vesterager | 128/635 |
| 4,379,454 | 4/1983 | Campbell et al. | 604/897 |
| 4,488,557 | 12/1984 | Engel | 128/635 |
| 4,517,982 | 5/1985 | Shiga et al. | 128/635 |
| 4,534,356 | 8/1985 | Papadakis | 128/635 |
| 4,536,274 | 8/1985 | Papadakis et al. | 204/433 |
| 4,653,498 | 3/1987 | New, Jr. et al. | 128/633 |
| 4,661,105 | 4/1987 | Gale | 604/897 |
| 4,685,464 | 8/1987 | Goldberger et al. | 128/633 |
| 4,687,481 | 8/1987 | Nuwayser | 604/897 |
| 4,692,462 | 9/1987 | Bannerjee . | |
| 4,725,272 | 2/1988 | Gale | 424/448 |
| 4,747,845 | 5/1988 | Korol | 604/368 |
| 4,764,382 | 8/1988 | Krydonieus et al. | 424/449 |
| 4,830,014 | 5/1989 | Goodman et al. | 128/665 |
| 4,847,260 | 7/1989 | Abe et al. | 514/279 |
| 4,849,226 | 7/1989 | Gale | 424/448 |
| 4,908,027 | 3/1990 | Enscore et al. | 604/890.1 |
| 4,926,867 | 5/1990 | Kanda et al. | 128/633 |
| 4,943,435 | 7/1990 | Baker et al. | 128/632 X |
| 5,007,423 | 4/1991 | Branstetter et al. | 128/633 |
| 5,267,563 | 12/1993 | Swedlow et al. | 128/665 X |

OTHER PUBLICATIONS

W. G. Zijlstra and G. A. Mook, Medical Reflection Photometry, pp. 50–77 (Royal VanGorcum Ltd.,) Assen, 1962).

*Primary Examiner*—Angela D. Sykes
*Attorney, Agent, or Firm*—Alisa A. Harbin; Steven F. Stone; Edward L. Mandell

[57] ABSTRACT

The present invention is directed to a sensor system for use with a blood characteristic measurement device such as a pulse oximeter, on areas of the body having low normal cutaneous blood flow and for monitoring a blood characteristic such as oxygen saturation and pulse rate of patients, preferably over an extended period of time. The sensor system includes (a) a transdermal device containing a blood perfusion-enhancing agent that is administered in a controlled amount to the skin of a human patient and (b) a skin surface sensor.

21 Claims, 2 Drawing Sheets

METHODS AND DEVICES FOR FACILITATED NON-INVASIVE OXYGEN MONITORING

This application is a continuation-in-part of application Ser. No. 07/722,645, filed Jun. 28, 1991, now U.S. Pat. No. 5,267,563.

FIELD OF THE INVENTION

The present invention is directed to the field of pulse oximetry. More particularly, this invention relates to the use of blood perfusion enhancers together with a skin surface sensor for improving the measurement and monitoring of a characteristic of a patient's blood, such as arterial oxygen saturation and pulse rate.

BACKGROUND OF THE INVENTION

The use of pulse oximeters to noninvasively measure a patient's heart rate and blood oxygen saturation is well known. In general terms, noninvasive measurement of blood oxygen saturation by a pulse oximeter typically requires the transcutaneous illumination of a portion of the patient's blood-perfused tissue by light at two or more wavelengths. Changes in the amount of blood in the tissue during a blood pressure pulse change the amount and character of the light detected by the sensor's photodetector. The amounts of light transmitted through the tissue at each wavelength may be compared to calculate to what degree the blood flowing through the tissue is saturated with oxygen. A more detailed discussion of the principles of pulse oximetry may be found in U.S. Pat. No. 4,653,498.

Pulse oximetry sensors fall into two general categories. Transmissive pulse oximetry sensors shine light through opposed blood perfused tissue surfaces, such as a finger or an ear, by disposing the light emitters and photodetectors on opposite sides of the tissue. Examples of such sensors are presented in U.S. Pat. Nos. 4,685,464 and 4,830,014. Transflectance sensors, on the other hand, emit light into and detect light from the same side of the tissue. An example of a transflectance sensor is the Nellcor Incorporated model RS-10 sensor.

With any pulse oximetry sensor, the quality of the measurement depends in part on the concentration of blood (relative to other tissue structures) in the portion of tissue illuminated by the sensor and in part on the magnitude of the pulsatile changes in the amount of blood in the tissue. Fingers are a preferred sensor site for transmissive sensors because of the fingers' relatively large number and concentration of blood vessels. However, well-perfused sites such as fingers are not always available. In addition, where it is desired to monitor the patient for an extended period of time, a sensor which is attached to a finger could be very awkward and inconvenient for the patient and could interfere with and restrict the patient's movements. Furthermore, movement of the sensor when the patient moves his or her hand could cause errors in the readings of the sensor. These situations could dictate the use of a transflectance sensor placed on the patient's torso, head, or some other part of the body that is convenient and accessible.

The torso, however, has a lower concentration of blood vessels near the skin surface than fingers have. In addition, blood flow to sensor sites on the torso or on any other part of the body may be restricted due to the effects of ambient temperature, systemically-acting vasoconstricting drugs in the patient's blood stream, or low patient blood pressure. The prior art has attempted to address this low perfusion problem in several ways.

Some prior art pulse oximeter sensors have used heaters to dilate the blood vessels at the sensor site, thereby increasing blood perfusion. See, e.g., U.S. Pat. Nos. 4,926,867 and 5,007,423. Heaters have also been used with other transcutaneous blood characteristic measuring devices, as shown in U.S. Pat. Nos. 3,628,525; 4,488,557; 4,324,256; 4,517,982; 4,534,356; 4,536,274; and Re. 31,440. The use of heaters raises the cost and complexity of the sensors, however, and presents the possibility of tissue burns.

An early oximeter sensor called the "Cyclops" is discussed in W. G. Zijlstra and G. A. Mook, Medical Reflection Photometry, pp. 50-77 (Royal VanGorcum Ltd., Assen, 1962). Unlike a pulse oximeter sensor (which distinguishes the arterial blood optical signal from the optical effects of venous blood and tissue by using only the AC component of the optical signal), the Cyclops sensor compared the optical signal from exsanguinated (i.e., bloodless) tissue with the optical signal from the tissue in a normal, blood-perfused state. Because the parameter of interest is the oxygen saturation of arterial blood, the Cyclops increased the ratio of arterial blood to venous blood in the tissue by "arterializing" the area through the iontophoretic application of histamine phosphate, a direct vasodilator and counterirritant. A voltage is applied to the patient's skin to drive the histamine phosphate into the tissue by a process called histamine iontophoresis.

Other transcutaneous blood characteristic measurement devices have used vasodilators to increase blood volume in the measuring region (U.S. Pat. Nos. 4,296,752, 4,488,557, and Re. 31,440). While these sensor systems do not require the use of iontophoresis, they do require the extra step of manually applying the chemical to the skin surface topically before a sensor is placed over the application area. In addition, none of these sensors is an optical sensor. The thick and irregular layer of chemicals these sensors use could adversely affect the optical performance of a pulse oximeter sensor through shunting, diffusion, reflectance or color shifting of the transmitted and received light.

Transdermal devices for the delivery of a drug to the skin have been known for some time, and representative systems which utilize rate-controlling membranes and in-line adhesives are disclosed in U.S. Pat. Nos. 3,598,122, 3,598,123, 3,742,951, 4,031,894, 4,060,084, 4,144,317, 4,201,211, 4,379,454 and 4,908,027, which are incorporated herein by reference.

A transdermal device for delivering certain vasodilators such as nitroglycerin is disclosed in U.S. Pat. Nos. 4,661,105, 4,725,272 and 4,849,226. These vasodilators are used to relieve the pain associated with angina pectoris, for the prevention of angina, in hypertension, for relaxation of involuntary muscles of blood vessels, for increasing the flow of blood therein and for increasing oxygenation from vasodilation, mainly for increasing the supply of oxygen to the heart. The transdermal device is designed to provide a higher dosage of the vasodilator through the skin to give the desired therapeutic result.

SUMMARY OF THE INVENTION

The unmet needs of the prior art are addressed by the present invention which provides a method and apparatus for simply and accurately measuring a blood characteristic such as blood oxygen saturation and pulse rate, particularly of an area of the body with a small concentration of blood vessels, by placing on an area of the body a sensor system for use with a blood characteristic measurement device, such as a pulse oximeter, which sensor system comprises 1) a transdermal delivery device for the local delivery of a blood perfusion enhancer and 2) a skin surface sensor.

In a preferred embodiment, the transdermal device is adapted to be placed on the active face of an electro-optical sensor and includes a backing member that is substantially impermeable to a blood perfusion-enhancing agent, an adhesive layer adjacent to the sensor-proximal surface of the backing member, a reservoir containing a blood perfusion-enhancing agent adjacent to the skin-proximal surface of the backing member, a rate-controlling membrane adjacent to the skin-proximal surface of the reservoir, and means for mating the transdermal device with a electro-optical sensor.

The invention is also directed to a method for accurately measuring blood characteristics such as oxygen saturation and pulse rate on areas of the body having low normal cutaneous blood flow and for monitoring the blood characteristic. This method comprises placing the sensor system of the invention so that the transdermal device is in perfusion-enhancing agent-transmitting relation with an area of the skin of the patient and the skin surface sensor is in optical communication with the skin, allowing the perfusion-enhancing agent to permeate the skin to cause increased blood flow in the localized area of the skin, and measuring the blood oxygen saturation and pulse rate with the sensor. This measurement may continue for an extended period of time.

The use of a transdermal delivery device uniquely allows a single step application of the perfusion-enhancing agent with attachment of the sensor.

BRIEF DESCRIPTION OF THE DRAWINGS

The drawings are not drawn to scale but are set forth for illustrating the invention.

DETAILED DESCRIPTION OF THE INVENTION

In accordance with this invention, there is provided a sensor system for use with a pulse oximeter for accurately measuring oxygen saturation and pulse rate on areas of the body having low normal cutaneous blood flow and for monitoring blood oxygen saturation and pulse rate of patients, preferably over an extended period of time. The sensor system includes (a) a transdermal device containing a blood perfusion-enhancing agent that is administered at a controlled amount to the skin of a human patient and (b) a skin surface sensor, such as an electro-optical sensor. The perfusion-enhancing agent increases locally the cutaneous blood flow for improving the performance of a pulse oximetry monitoring system.

The term "transdermal" delivery or application as used herein refers to the delivery or application of agents by passage through skin, mucosa and/or other body surfaces by topical application.

The term "extended period of time" as used herein refers to a period of time of at least one hour. Preferably, it refers to a period of time of at least several hours, and more preferably, from about eight hours to three days and can be for periods of up to about seven days.

Figure 1:
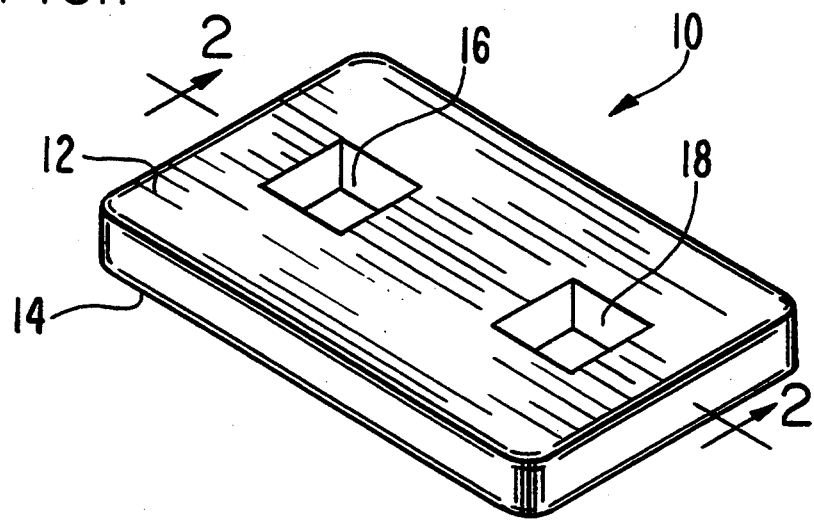
FIG. 1 illustrates in top view a transdermal perfusion enhancer delivery device according to the invention.

FIG. 1 is a top view of one embodiment of the transdermal device 10 of the invention, which is designed and adapted for easy placement and comfortable retention on the skin and for easy placement and retention on a surface sensor probe of a pulse oximeter. Device 10 has a sensor side 12 and a skin side 14. An emitter window 16 and a detector window 18 are positioned in the device 10 so that they will line up with the light emitter and the photodetector of the pulse oximeter sensor when the sensor is placed in position over the transdermal device. The emitter window 16 and the detector window 18 in a presently preferred embodiment are holes which have been cut, punched or otherwise formed and which extend through the entire thickness of the device 10.

Transdermal device 10 can be shaped and sized for placement and retention on various anatomic regions for cutaneous administration of a blood perfusion enhancer to a patient. The anatomic regions are those to which the surface sensor of the invention is adapted for use and are represented by the forearm, abdomen, chest, back, thigh, buttock, and the like. Transdermal device 10 can have various shapes, such as oblong, square, rectangular, round, and the like. For example, two or more devices, shaped as strips for example, may be placed in position on each side of or around the light emitter and the photodetector of the sensor, eliminating the necessity for windows in the device. However, it is preferred that device 10 be of a shape that conforms to the shape of the active face of the surface sensor with which it is adapted to be used.

Figure 2:
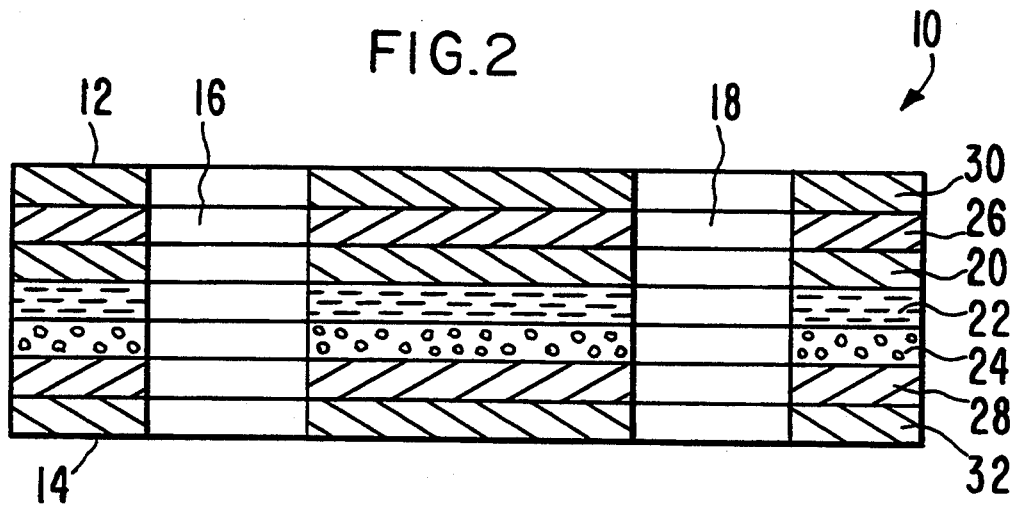
FIG. 2 is a cross-sectional view of the transdermal device of FIG. 1, along line 2—2.

FIG. 2 shows device 10 of FIG. 1 in cross-sectional view through line 2—2 for illustrating the structure of device 10. Device 10 includes a backing member 20 on the sensor side 12 of the device. A reservoir 22, adjacent to backing member 20, is positioned immediately below and in contact with the surface of backing member 20 that is proximal to the skin side 14 of the device. Reservoir 22 contains a blood perfusion enhancer that is to be delivered to the skin. Device 10 also includes rate-controlling membrane 24 for controlling the release of the perfusion enhancer from the device. Rate-controlling membrane 24 has one surface in contact with the skin-proximal surface of reservoir 22.

Transdermal device 10 further includes a first adhesive layer or lamina 26 in contact with the sensor-side surface of backing member 20 and a second adhesive layer or lamina 28 in contact with the skin-side surface of rate-controlling membrane 24. First adhesive layer 26 is present for the purpose of adhering device 10 to the active face of a pulse oximeter surface sensor. Second adhesive layer 28 is used for affixing device 10 and the surface sensor as a sensor system to an area of skin of a patient. The composition and the thickness of second adhesive layer 28 are such that layer 28 does not constitute a significant permeation barrier to the passage of the blood perfusion enhancer, and it should preferably be substantially more permeable to the passage of perfusion enhancer than rate-controlling membrane 24, and it is at least as permeable to perfusion enhancer as membrane 24. The adhesives used in layers 26 and 28 may be the same or different. The adhesive used for at least layer 28 is dermatologically acceptable and it permits the device to be easily removed from the skin after the measurement of oxygen saturation and pulse rate is completed.

Transdermal device 10 also may include a first release liner 30 in contact with first adhesive layer 26 and a second release liner 32 in contact with second adhesive layer 28. Release liners 30 and 32 protect device 10, and they are removed just prior to use of the device.

Emitter window 16 of device 10 extends throughout all of the layers of the device, for providing passage of the light emitted from the sensor's emitter. Detector window 18 likewise extends throughout all of the layers of the device, for allowing the sensor's photodetector to detect the light passing through the skin from the sensor's emitter. Windows in release liners 30 and 32 are not necessary to the operation of the device, of course, since the liners are removed before application to the patient. In order to eliminate any reflectance or shunting of the emitted light in the device itself, which will affect the calibration of the pulse oximeter, it is preferred that the device be opaque to the wavelengths of light used by the oximeter. This may be most easily accomplished by having one or the other or both of backing membrane 20 and reservoir 22 be of an opaque material, such as a black or other dark-colored material that will absorb any light that may stray into the device.

Materials which may be used for backing member 20 are chosen from those materials that are substantially impermeable to the components in device 10. These may be single materials or a combination of materials such as a composite or a laminate. The material may be occlusive or non-occlusive, flexible or non-flexible. Examples of materials that can be used as backing member 20 are polymeric materials such as low to high density polyethylene, polypropylene, polyethylene terephthalate, nylon, and the like. Other materials are known in the art, examples of which are listed in the transdermal device patents discussed earlier herein.

The reservoir 22 of the transdermal device of this invention contains a saturated or unsaturated formulation of the blood perfusion-enhancer. A suitable formulation may be aqueous or non-aqueous based. The formulation should be designed to deliver the perfusion enhancer at the necessary flux. Aqueous formulations typically comprise water or water/ethanol and about 1-2 wt % of a gelling agent, an example being a hydrophilic polymer such as hydroxyethylcellulose or hydroxypropylcellulose. Typical non-aqueous gels are comprised of silicone fluid or mineral oil. Mineral oil-based gels also typically contain 1-2 wt % of a gelling agent such as colloidal silicon dioxide. The suitability of a particular gel depends upon the compatibility of its constituents with the perfusion enhancer and any other components in the formulation.

The reservoir 22 preferably comprises a matrix containing the blood perfusion enhancer, and the matrix should be compatible with the perfusion enhancer and any carrier therefor. The term "matrix" as used herein refers to a well-mixed composite of ingredients fixed into shape. When using an aqueous-based formulation, the reservoir matrix is preferably a hydrophilic polymer, e.g., a hydrogel. When using a non-aqueous-based formulation, the reservoir matrix is preferably composed of a non-hydrogel polymer. Suitable polymeric matrices are well known in the transdermal drug delivery art, and examples are listed in the above-named patents previously incorporated herein by reference.

A typical laminated system would comprise a polymeric matrix such as ethylene vinyl acetate (EVA) copolymers, such as those described in U.S. Pat. No. 4,144,317, preferably having a vinyl acetate (VA) content in the range of from about 9% up to about 60% and more preferably about 28% to 60% VA. Polyisobutylene/oil matrices containing from 4-25% high molecular weight polyisobutylene and 20-81% low molecular weight polyisobutylene with the balance being an oil such as mineral oil or polybutynes may also be used.

The blood perfusion-enhancing agent useful in the present invention is chosen from those agents which can enhance the perfusion, or passage, of blood through a vascular bed. Examples of perfusion-enhancing agents include local skin irritants, vasodilators, and counterirritants such as methyl salicylate and menthol. One presently preferred class of perfusion-enhancing agents are the vasodilators, which are delivered to induce a localized vasodilation of cutaneous blood vessels. This vasodilation results in an increase of the local cutaneous blood flow which is visible as an erythema. Among the vasodilators, a preferred group of perfusion enhancers are nicotinic acid and the lower alkyl esters of nicotinic acid, such as methyl nicotinate and hexyl nicotinate. Additional examples of vasodilators are sodium salt of nicotinic acid, nicotinyl alcohol, benzyl nicotinate and thurfuryl nicotinate. Mixtures of vasodilators are also contemplated. The term "lower alkyl" as used herein refers to alkyl groups, straight-chained or branched, of one to six carbon atoms. Nicotinic acid esters, where the esters are alkyls of five or more carbons, are known permeation enhancers (U.S. Pat. No. 4,847,260), but none of the presently contemplated vasodilators are known to be delivered alone from a transdermal device for inducing or enhancing localized perfusion or to be used with a pulse oximeter surface sensor for facilitating measurement of oxygen saturation and pulse rate.

The perfusion enhancer is present in the reservoir of the transdermal device in a perfusion-enhancing amount, that is, an amount sufficient to provide a perfusion-enhancing effect for the entire useful life of the device or, in other words, for the entire extended period of time during which the device is used with the surface sensor to measure the oxygen saturation and the pulse rate or other characteristics of a patient's blood. The minimum amount of perfusion enhancer is determined by the requirement that sufficient quantities of enhancer must be present in the device to maintain the desired rate of release over the given, predetermined period of application. The amount of perfusion enhancer in the reservoir generally ranges from about 0.1 wt % (percent by weight) to about 70 wt % or greater but may be any amount which provides a perfusion-enhancing effect for the desired extended period of time. When the perfusion enhancer is a vasodilator such as nicotinic acid or lower alkyl esters of nicotinic acid, the amount is generally from about 0.1 wt % to about 50 wt %, but may be greater.

The perfusion-enhancing rate of delivery of the vasodilator to the skin should be great enough to cause a local vasodilation of the blood vessels and increased blood flow, as manifested by a local erythema, but not so great as to cause detectable build-up of the vasodilator in the systemic circulation of the patient's body.

Additionally, if the concentration of the vasodilator in the cutaneous region is too high, edema as well as erythema can result. This is undesirable because the presence of edema on a patient's skin will cause the readings of the surface sensor to be incorrect. The preferred vasodilators readily permeate through human skin so that the use of a rate-controlling membrane to control the rate of release of the vasodilators is generally required. The preferred perfusion-enhancing release rate of the vasodilators to the skin of a patient from the transdermal device is generally from about 0.5 $\mu g/cm^2$-hr to about 500 $\mu g/cm^2$-hr at 37° C., and is preferably from about 5 $\mu g/cm^2$-hr to about 200 $\mu g/cm^2$-hr. In a presently preferred embodiment, the vasodilator is methyl nicotinate.

Rate-controlling membrane 24 is selected from a release rate-controlling material for governing the amount of blood perfusion enhancer released from transdermal device 10. Membrane 24 is formed of a material that permits the passage of perfusion enhancer at a rate dependent on the solubility of the enhancer therein, as well as on the thickness of the membrane. The flux rate of the enhancer is thus controlled to the exterior of the device 10 by regulating the composition and thickness of rate-controlling membrane 24 and the diffusion coefficient of the enhancer; thus, device 10 can be provided with the same surface area and having different rates of perfusion enhancer release by varying the characteristics of membrane 24. Diffusion coefficients can be determined by standard techniques. The membrane is selected to deliver perfusion enhancer at a rate less than the permeability of average skin in order to provide the low perfusion-enhancing rate required by this invention. Rate-controlling membrane 24 also assures the constant maintenance of a controlled release rate over an extended period of time. Representative materials for forming rate-controlling membrane 24 are generally chosen from polymers and include polyolefins such as polyethylene, high density polyethylene, and polypropylene; polyamides; polyesters; ethylene-ethacrylate copolymer; segmented copolymer of butylene terephthalate 33% and polytetramethylene ether terephthalate 67%; segmented copolymer of propylene terephthalate 58% and polytetramethylene ether terephthalate 42%; block copolymer of tetramethylene terephthalate-polytetramethylene ether glycol terphthalate; ethylene-vinyl acetate copolymer; ethylene-vinyl methylacetate copolymer; ethylene-vinyl ethylacetate copolymer; ethylene-vinyl propylacetate copolymer; polyisoprene; polyacrylonitrile; ethylene-propylene copolymer; and the like.

First adhesive layer 26 can be selected from any contact adhesive which will provide sufficient adhesion of the transdermal device 10 to the surface sensor during the entire period of time the sensor and the device are being worn by the patient. Where the surface sensor is reusable, that is it will be used repeatedly on different patients, the adhesive should not be so strong that the device 10 cannot be readily removed from the sensor. Suitable contact adhesives are known in the art and are readily available. The first adhesive 26 may be the same as or different from the second adhesive 28.

Second adhesive layer 28 should be chosen from adhesives that are essentially free of the property of stripping skin cells upon the removal of the device 10 from the patient. Representative adhesives are known in the art and include, but are not limited to, a mixture of 2-cyanoacrylate and dimethyl methylenemalonate, monomeric esters of alpha-cyanoacrylic acid, cross-linked copolymers of dimethylaminoethylmethacrylate and an alkyl acrylate, an adhesive composition comprising a hydrocolloid gum, polyisobutylene, polyisobutylene and cross-linked dextran, silicone medical adhesive, mineral oil-polyisobutylene, polyisobutylene-polybutynes, and the like.

In a preferred embodiment of the invention, increased perfusion sufficient for an accurate measurement of oxygen saturation is obtained within about five minutes after application of the transdermal device to the skin of a patient. To provide this quick onset of enhanced perfusion, second adhesive layer 28 can optionally contain an initial amount of the perfusion-enhancing agent which is released therefrom as an initial dose, with the device thereafter delivering the perfusion enhancer at a substantially constant rate during the duration of the measurement period. The amount of perfusion enhancer in the adhesive is generally from about 0.1 wt % to about 70 wt %.

The first release liner 30 in contact with first adhesive layer 26 and the second release liner 32 in contact with second adhesive layer 28 are exemplified by, in one embodiment, the same materials used for the backing member 20, provided they are removable or made removable by siliconizing or otherwise treating the material. Other release liners include, but are not limited to, siliconized polyester, fumed silica in silicone rubber, end-capped siliconized polyethylene terephthalate, polytetrafluoroethylene, cellophane, treated paper, siliconized paper, aluminized paper, paper coated with polyethylene, a film of polyvinyl chloride having titanium dioxide dispersed therein, and the like as are known in the art.

The devices of this invention can be designed to effectively deliver a blood perfusion-enhancing agent for an extended time period of from about one hour up to 7 days or longer. Seven days is generally the maximum time limit for application of a single device because the skin site is often adversely affected when occluded for a period greater than 7 days.

The transdermal therapeutic devices of the present invention are prepared as described herein and in a manner generally known in the art, such as by those procedures, for example, described in the transdermal device patents listed previously herein and incorporated by reference.

Figure 3:
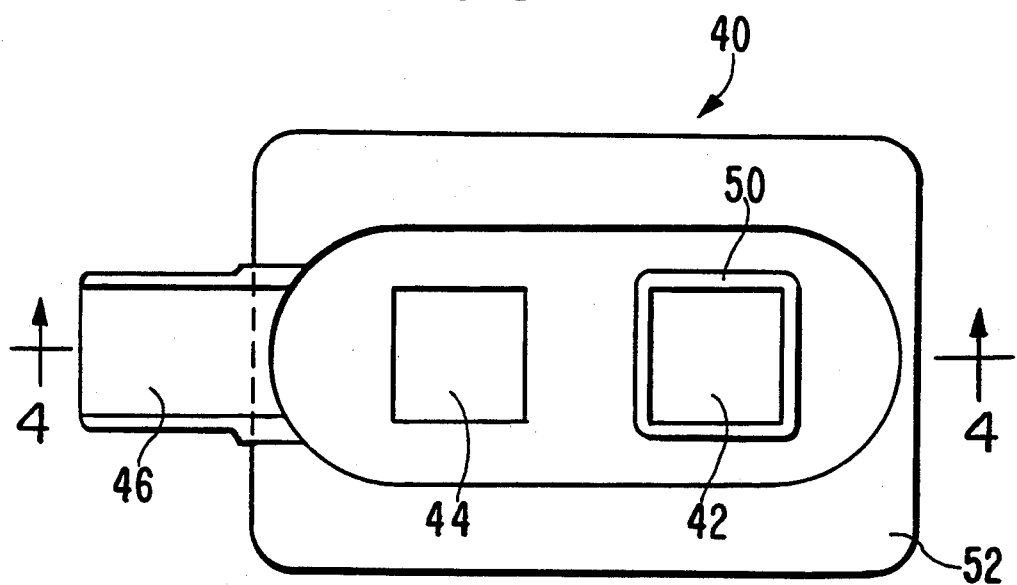
FIG. 3 is an elevational view of the active face of a sensor for use with the transdermal device of FIGS. 1 and 2.

The preferred surface sensor for use with the system of this invention is a pulse oximeter sensor as shown in FIG. 3. Sensor 40 is a modified Nellcor Incorporated RS-10 surface sensor. The sensor's light sources 42 are preferably a red LED and an infrared LED. The sensor also includes a conventional large area photodetector 44. Photodetector 44 is preferably covered by a grounded Faraday shield (not shown). LEDs 42 and photodetector 44 are connected to sensor cable 46 by suitable conductors (not shown). LEDs 42 and photodetector 44 are covered by epoxy domes 48.

Figure 4:
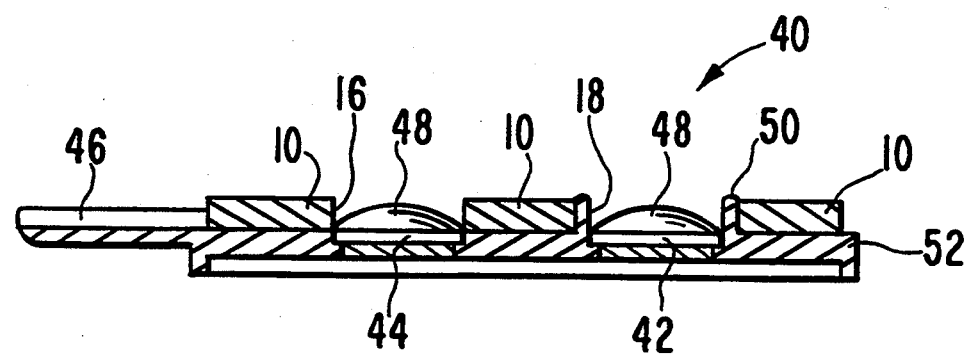
FIG. 4 is a cross-sectional view of the sensor of FIG. 3, along line 4—4, on which a transdermal device according to this invention has been mounted.

A planar surface 52 on sensor 40 provides a platform for transdermal device 10. As shown in FIG. 4, the epoxy dome 48 covering LEDs 42 is surrounded by a ridge 50 that is designed to extend through the emitter window 16 of device 10. Ridge 50 minimizes optical shunting between LEDs 42 and photodetector 44 through transdermal device 10. Alternatively, a ridge can be formed around photodetector 44 and extending through detector window 18 of device 10. Other means of reducing optical shunting will be apparent to those skilled in the art. In addition, other electro-optical sensors, such as a heart rate sensor or an electro-chemical sensor, may be used in place of the pulse oximeter sensor without departing from the scope of the invention.

The sensor system of the present invention for use with a pulse oximeter comprises in a presently preferred embodiment a transdermal delivery device for the local delivery of a blood perfusion enhancer, as described above, and a pulse oximeter sensor, as also described above. One embodiment of a system of the invention is shown in cross-section in FIG. 4. The transdermal device is adhered to the active face of the sensor to form the sensor system, and the sensor system is then affixed to the skin of a patient. Alternatively, the transdermal device is first applied to a predetermined site on the patient's skin and the active face of the sensor is then adhered to the transdermal device. While the sensor system may be applied to any suitable portion of the body, in a preferred embodiment the system is placed on an area having a low normal cutaneous blood flow such as the torso, and more preferably on the back, stomach or chest. After placement on the skin, the transdermal device delivers a blood perfusion enhancer at a constant, perfusion-enhancing rate to obtain a localized increase of the cutaneous blood flow. Once perfusion has been increased, the surface sensor will begin to accurately measure and monitor the oxygen saturation and the pulse rate of the patient for an extended period of time of from about one hour to three days or longer.

The following examples are presented to further illustrate the apparatus and method of the present invention. The examples are not intended to limit the invention in any manner.

EXAMPLE 1

Transdermal devices according to the invention were prepared as follows.

Ethylene-vinyl acetate copolymer pellets (40% vinyl acetate; "EVA 40") (247 g) were pre-blended for approx. 6 min. at 58° C. and 30 rpm. Methyl nicotinate (1.13 g) was slowly added to the EVA 40 over a period of 6 min. with mixing at the same speed. Then, the two ingredients were mixed uniformly at 78° C. and 40 rpm for 20 min.

The EVA 40/methyl nicotinate mixture was placed in an extruder (with 3-to-1 compression screw and 4-in. die) and a matrix 15 mils thick and 5 in. wide was extruded. The extruder was operated at 80° C. at all zones, under 1,050 psi pressure and at a screw speed of 93 rpm. The matrix, together with a 2 mil thick EVA 9 film and a pigmented medium density polyethylene ("MDPE") film, was then passed through a calendar/laminator, set at the speed of 0.45 ft/min, roll gap of 17.5 mils, roll temperature of 78° C. and roll pressure of 90 psi, to produce a tri-laminate of EVA 9 (as the rate-controlling membrane), EVA 40/methyl nicotinate, and MDPE (as the backing of the system). The tri-laminate was cut into 12-in. sections, and 2 mil thick acrylic adhesive film on a release liner was laminated to each of the MDPE film side and the EVA 9 rate-controlling membrane side of the tri-laminate sections, using the calendar/laminator set at 40 psi. The final weight fraction of methyl nicotinate in the multilaminate, whose cross-section is depicted in FIG. 2, was about 0.3 wt %, excluding the release liners.

The sheet of multilaminate was cut into pieces of 1 in. × ⅜ in. size (to fit on the planar surface of a sensor). Two square holes were cut out of each transdermal device corresponding to the position of the sensor's light emitters (LEDs) and photodetector, to give methyl nicotinate transdermal devices.

Following the above procedures, transdermal devices containing 0.6 wt % or 0.8 wt % of methyl nicotinate were also prepared.

EXAMPLE 2

The methyl nicotinate devices of Example 1 were tested with a modified pulse oximeter surface sensor, as illustrated in FIG. 3, on healthy adults to determine the accuracy of oxygen saturation and pulse rate measurements on areas of the body having a low normal cutaneous blood flow.

A Nellcor N200 pulse oximeter was used, and signals were collected using a Toshiba T5200 "datasys" program. The surface sensor used, generally illustrated in FIG. 3, housed a red LED and an IR LED and also a large area photodetector with a Faraday shield configured in a black PVC shell. The skin contact, or active, side of the sensor shell was winged to provide maximum contact area with the transdermal device and the skin.

A 0.6 wt % methyl nicotinate device from Example 1 was placed, via the contact adhesive at the backing surface of the device, onto the active face of the sensor, with the holes in the device positioned over the light emitter and the photodetector of the sensor. A device and sensor were placed on the chest, adjacent to the sternum between ribs 2 and 3, on each of 12 subjects. A placebo device, without methyl nicotinate, and sensor were also placed on each individual. The test was performed over a 30 min period.

In every case, the test sensor locked on anywhere from initial application up to 6 min after application. "Lock on" is displayed heart and oxygen saturation readings on the pulse oximeter instrument front panel. The placebo sensor, on the other hand, rarely locked on but repeatedly found the respiration rate and displayed erroneous pulse and oxygen rates. Thus, the methyl nicotinate delivery system enhanced the modulation signal to provide a means for monitoring oxygen saturation on the torso.

EXAMPLE 3

Following the procedures of Example 1, devices for attachment to a surface sensor of a pulse oximeter and for the delivery of methyl nicotinate were prepared having the following composition.

The backing was clear polyethylene terephthalate and had a thickness of 2 mils; the reservoir was 50 wt % methyl nicotinate and 0.1–1.0 wt % carbon black powder in EVA 40 and had a thickness of 5–10 mils; the rate-controlling membrane was high density polyethylene and had a thickness of 2–3 mils; the first and second adhesive layers were polyisobutylene and had a thickness each of 1.5–2.5 mils; and the release liners were siliconized polyethylene terephthalate.

Having thus generally described the present invention and described certain specific embodiments thereof including the embodiments that the applicants consider the best mode of practicing their invention, it will be readily apparent that various modifications to the invention may be made by workers skilled in the art without departing from the scope of this invention which is limited only by the following claims.

What is claimed is:

1. A transdermal delivery device for facilitating the non-invasive monitoring of a characteristic of a patient's blood vessels, wherein the device consists essentially of:
   (a) a backing member that is substantially impermeable to a perfusion-enhancing agent;
   (b) a first adhesive layer adjacent to the skin-distal surface of the backing member;
   (c) perfusion agent reservoir means adjacent to the skin-proximal surface of the backing member; and
   (d) means for maintaining said reservoir in perfusion agent transmitting relationship to the skin of the patient.

2. A device according to claim 1 wherein said maintaining means comprises a second adhesive layer.

3. A device according to claim 1 wherein the device is opaque.

4. A device according to claim 1 wherein the perfusion-enhancing agent is a vasodilator.

5. A device according to claim 4 wherein the vasodilator is selected from nicotinic acid and lower alkyl esters of nicotinic acid.

6. A device according to claim 1 wherein the perfusion-enhancing agent is methyl nicotinate.

7. A device according to claim 1 wherein the device further comprises an emitter window and a detector window.

8. A device according to claim 1 wherein the perfusion-enhancing agent is methyl nicotinate, and the device further comprises a second adhesive layer adjacent to the skin-proximal surface of the rate-controlling membrane, an emitter window and a detector window.

9. A device according to claim 1 wherein the perfusion-enhancing agent is a counterirritant.

10. A device according to claim 1 wherein said device further comprises a rate controlling membrane adjacent to the skin proximal surface of said reservoir means.

11. A transdermal delivery device for delivering a perfusion-enhancing agent to a human at a substantially constant rate over an extended period of time to obtain a localized increase of the cutaneous blood flow, wherein the device consists essentially of:
   (a) a backing member that is substantially impermeable to a perfusion-enhancing agent;
   (b) a first adhesive layer adjacent to the skin-distal surface of the backing member;
   (c) a perfusion agent reservoir means adjacent to the skin-proximal surface of the backing member; and
   (d) means for maintaining said reservoir in perfusion agent transmitting relationship to the skin of the patient.

12. A device according to claim 11 which further comprises an emitter window and a detector window.

13. A device according to claim 11 wherein said maintaining means comprises a second adhesive layer.

14. A device according to claim 11 wherein the device is opaque.

15. A device according to claim 11 wherein the perfusion-enhancing agent is a vasodilator.

16. A device according to claim 15 wherein the vasodilator is selected from nicotinic acid and lower alkyl esters of nicotinic acid.

17. A device according to claim 11 wherein the perfusion-enhancing agent is methyl nicotinate.

18. A device according to claim 11 wherein the perfusion-enhancing agent is methyl nicotinate, and the device further comprises a second adhesive layer adjacent to the skin-proximal surface of the rate-controlling membrane, an emitter window and a detector window.

19. A device according to claim 11 wherein the perfusion-enhancing agent is a counterirritant.

20. A device according to claim 11 wherein the extended period of time is from 8 hours to 3 days.

21. A device according to claim 11 wherein said device further comprises a rate controlling membrane adjacent to the skin proximal surface of said reservoir means.

* * * * *